(12) United States Patent
De Carle

(10) Patent No.: US 6,685,315 B1
(45) Date of Patent: Feb. 3, 2004

(54) BIFOCAL LENSES

(76) Inventor: John Trevor De Carle, Lowicks House, Tilford, Surrey (GB), GU10 2EX ( * ) Notice: Subject to any disclaimer, the term of this patent is extended or adjusted under 35 U.S.C. 154(b) by 0 days.

(21) Appl. No.: 10/070,498

(22) PCT Filed: Sep. 1, 2000

(86) PCT No.: PCT/GB00/03369
§ 371 (c)(1),
(2), (4) Date: Jun. 17, 2002

(87) PCT Pub. No.: WO01/18592
PCT Pub. Date: Mar. 15, 2001

(30) Foreign Application Priority Data

Sep. 3, 1999 (GB) ............................................... 9920882
Nov. 26, 1999 (GB) ............................................... 9928027

(51) Int. Cl.⁷ .................................................. G02C 7/04
(52) U.S. Cl. ........................................ 351/161; 351/177
(58) Field of Search ........................ 351/160 R, 160 H, 351/161, 162, 177

(56) References Cited

U.S. PATENT DOCUMENTS

| 5,116,111 A | * | 5/1992 | Simpson et al. | 351/161 |
| 5,225,858 A | * | 7/1993 | Portney | 351/161 |
| 5,798,817 A | * | 8/1998 | de Carle | 351/161 |
| 6,007,201 A | * | 12/1999 | Wada et al. | 351/161 |

* cited by examiner

Primary Examiner—Scott J. Sugarman
(74) Attorney, Agent, or Firm—Michael Y. Epstein

(57) ABSTRACT

Bifocal contact and intraocular lenses are described wherein a viewing area which has an extend generally corresponding to the maximum pupil area of the wearer, said viewing area having a central circular refractive zone having a first focal length corresponding to distance or reading vision, and a plurality of annular, concentric refractive zones which alternate between a second focal length corresponding to the other of reading and distance vision and said first focal length as they extend outwardly from said central zone, wherein the total number of said zones is at least 20. Preferably, at least one of the zones has a power which is more negative than a zone of the same character which is situated closer to the center of the lens.

14 Claims, 3 Drawing Sheets

BIFOCAL LENSES

Figure 1:
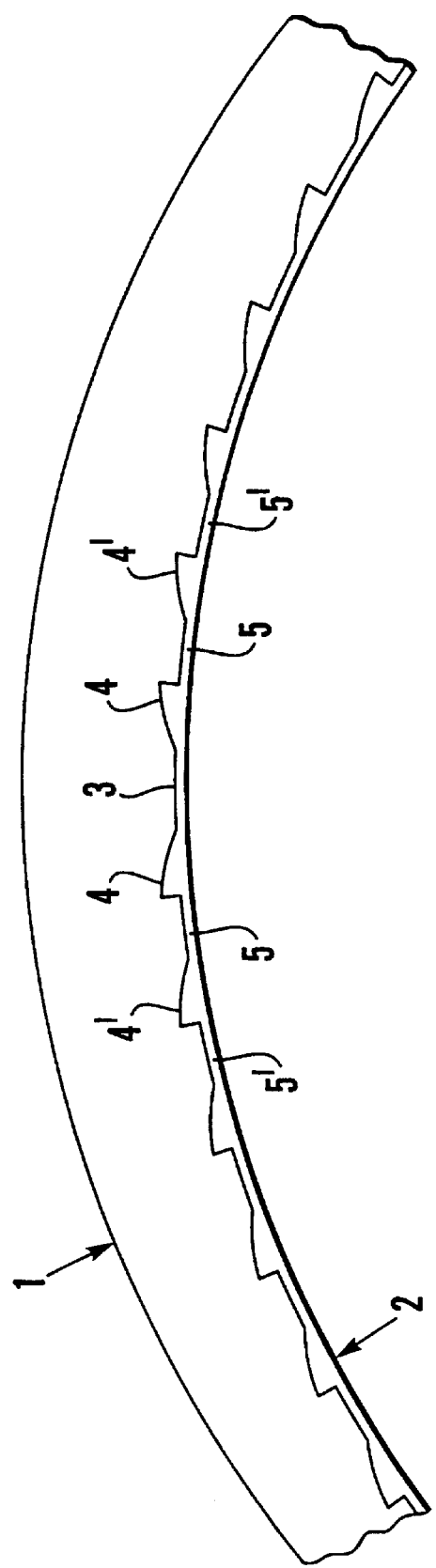

This invention relates to bifocal lenses and in particular to bifocal and trifocal contact and intraocular lenses.

Various designs of bifocal contact lenses have been proposed but all require considerable amounts of chair-side time for satisfactory fitting of such lenses. Designs have been proposed in which the viewing area consists of a central circular zone, surrounded by concentric zones of alternating near (reading) and distant vision. U.S. Pat. No. 4,890,913 discloses such a lens. The underlying concept in the above patent is to try to ensure that at every pupil size the amount of light transmitted through the reading and distant vision zones is substantially equal. It has been found that with such lenses when correctly fitted, the wearer is able to concentrate on the clearest image focused on the retina.

While the lenses described in the above U.S. patent have made a useful contribution to the art, and can reduce the amount of fitting time required, there are still some problems to be overcome. Lenses manufactured in accordance with the above patent are most effective when manufactured as hard lenses, or from lens material which have a low water content. If, on the other hand, lenses are made in accordance with the prior patent in a soft, high water content lens material, the zones formed on a posterior lenticular surface tend to be "ironed out" by the pressure of the upper eyelid.

Another, unrelated problem of some prior art lenses, is that in certain light conditions, reflections are seen from junctions between adjacent zones. This can have the effect of giving the appearance of rings around a light source.

The present invention is, therefore, in one aspect directed to a solution to the above problems and the provision of a lens which can be used both as a contact lens, and as an intraocular lens from a variety of conventional lens materials.

According to the present invention there is provided a contact or intraocular bifocal lens comprising a viewing area which has an extent generally corresponding to the maximum pupil area of the wearer, said viewing area having a central circular refractive zone having a first focal length corresponding to either distance or reading vision, and a plurality of annular, concentric refractive zones which alternate between a second focal length corresponding to the other of reading and distance vision and said first focal length as they extend outwardly from said central zone, wherein the total number of zones is at least 20. Preferably, the central circular zone has a focal length corresponding to distance vision.

The provision of a very large number of alternating reading and distance zones in the viewing area is believed to be responsible for overcoming many of the problems of the prior art lenses. One significant advantage is that by providing a large number of zones, it is much easier to ensure that the relative areas of the distance and reading zones is close to the preferred 50:50 ratio at all pupil sizes. As a consequence, the lenses provide good distance and reading vision in all lighting conditions. The number of zones is at least 20 and is preferably much higher, e.g. at least 30 and preferably at least 50. A typical number of zones may be between 20 and 50, e.g., 25 to 40. There is no theoretical upper limit but there will be a practical upper limit which is determined by the limitations of the equipment or system used to form very large numbers of zones on the surface of a lens. Existing computer controlled lathes should be capable of forming up to about 70~80 alternate zones on the lenticular surface of a standard contact lens, in which the major viewing area is about 6~8 mm in diameter.

The alternating zones may be formed on the front surface of the lens, but are preferably formed on the rear surface of the lens. One advantage of forming the zones on the posterior surface of the lens is that any imperfection in the surface is largely compensated by the tear fluid which will fill the space between the undulating profile forming the zones and the cornea.

Preferably, the maximum tear thickness between the anterior lens surface and the cornea is about 0.007 mm and may be as little as 0.003 mm.

In general, the maximum thickness of material removed between every other zone to form the zones is about 10% of the total thickness of the lens.

Another, separate problem arises in fitting bifocal contact lenses. This relates to the observation that eyes suffer from the fact that the combined power of the cornea and the natural crystalline lens increases towards the periphery. As a result, when the pupil dilates in low lighting conditions, a patient with normal distance vision will experience improved distance vision when wearing corrective lenses with a negative power of about 0.5 dioptres.

Another aspect of the present invention is based on the realisation that improved vision with bifocal lenses can be achieved by introducing a progressive power variation in a multi-zonal concentric lens in which the negative power of one or both types of vision zones is increased towards the periphery of the viewing area of the lens. Such progression in negative power should not exceed about 1 dioptre, preferably not more than about 0.75 to 0.8 dioptre and, generally, will be in the range of 0.25 to 0.75 dioptre. A power change of about −0.5 dioptre from centre to periphery being preferred.

According to a further aspect of the present invention, therefore, there is provided a bifocal contact lens wherein, at least, the major viewing area is divided into a plurality of near and distance vision zones which are formed as annular zones of different radii from a point in the region of the centre of the lens, each near vision zone being adjacent to a distance vision zone or intermediate vision zone and, wherein at least one of the zones has a power which is more negative than a zone of the same character which is situated closer to the centre of the lens. Lenses in accordance with this aspect of the invention do not necessarily have a larger number of alternating zones as described above. However, in a preferred embodiment, the number of zones is at least 20 and often up to 70 or 80.

Preferably, at least one distance vision zone has a power which is more negative than a distance vision zone situated closer to the centre of the lens. Generally, the distance vision zones have powers which progressively become more negative towards the periphery of the lens viewing area so that the zones towards the periphery have the highest degree of negative power.

In general, there is no further increase in clarity by increasing the negative power by more than about 1 dioptre. Normally, the increase in negative power will be limited to 0.75 to 0.8 dioptre. Usually, optimum benefit is obtained where the negative power increase is in the region of 0.5 to 0.6 dioptre. The maximum additional negative power at the periphery is limited by the onset of reverse spherical aberration.

In the manufacture of lenses in accordance with both aspects of the invention, the zones may be formed by machining the power or base curve of the lens. Preferably, however, the power is produced by machining or moulding the power surface of the lens. In order to provide a smooth transition between zones, it is preferable to make the zones at least partially aspherical, generally by making some or all of the near vision zones aspherical, so that aspherical lens surfaces merge smoothly into spherical lens surfaces with minimum discontinuity at the junction between two zones. Lenses produced in accordance with this concept are described in UK Patent Application No. 2,295,686 (de Carle), and the content of this prior UK specification is specifically incorporated herein.

It may also be advantageous to manufacture lenses in accordance with the invention in such a way that the optical centre of at least the major viewing part of the lens is displaced by a small distance from the geometric centre of the lens. The displacement is such that when the lenses are worn, the lens is offset nasally on the cornea. This concept is described in PCT/WO 98/53360 (de Carle) and in European Patent Application No. 0618474 (Menicon), and the subject-matter of these specifications is specifically incorporated herein.

In accordance with the second aspect of the invention, some or all of the zones may be provided by diffraction as described in U.S. Pat. No. 4,637,697 (Freeman). Lenses in accordance with the first aspect of the invention generally operate by refraction.

Figure 2:
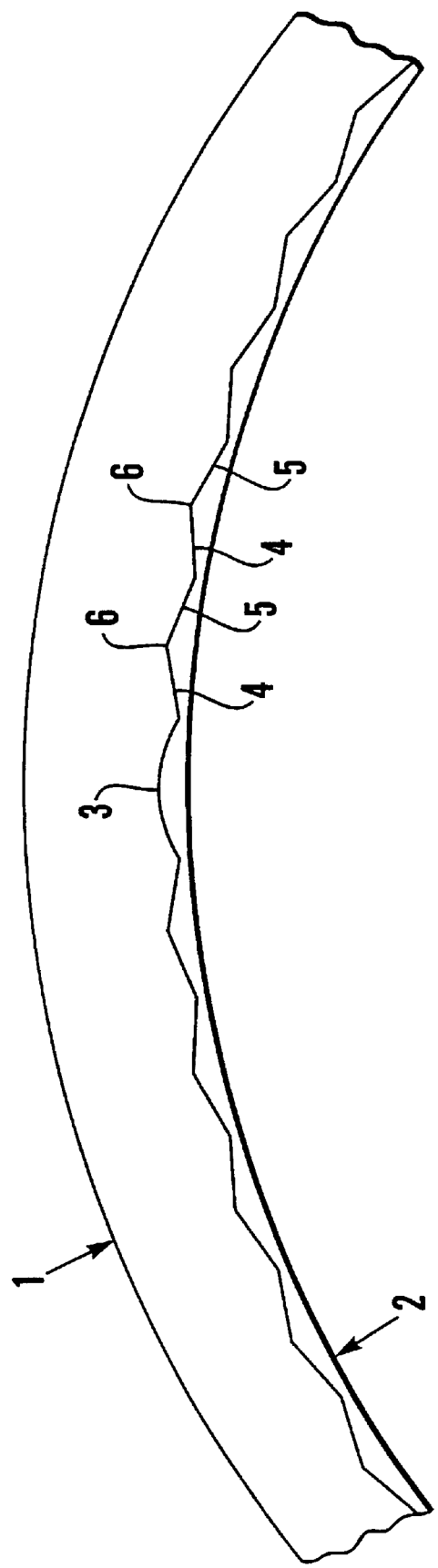
Figure 3:
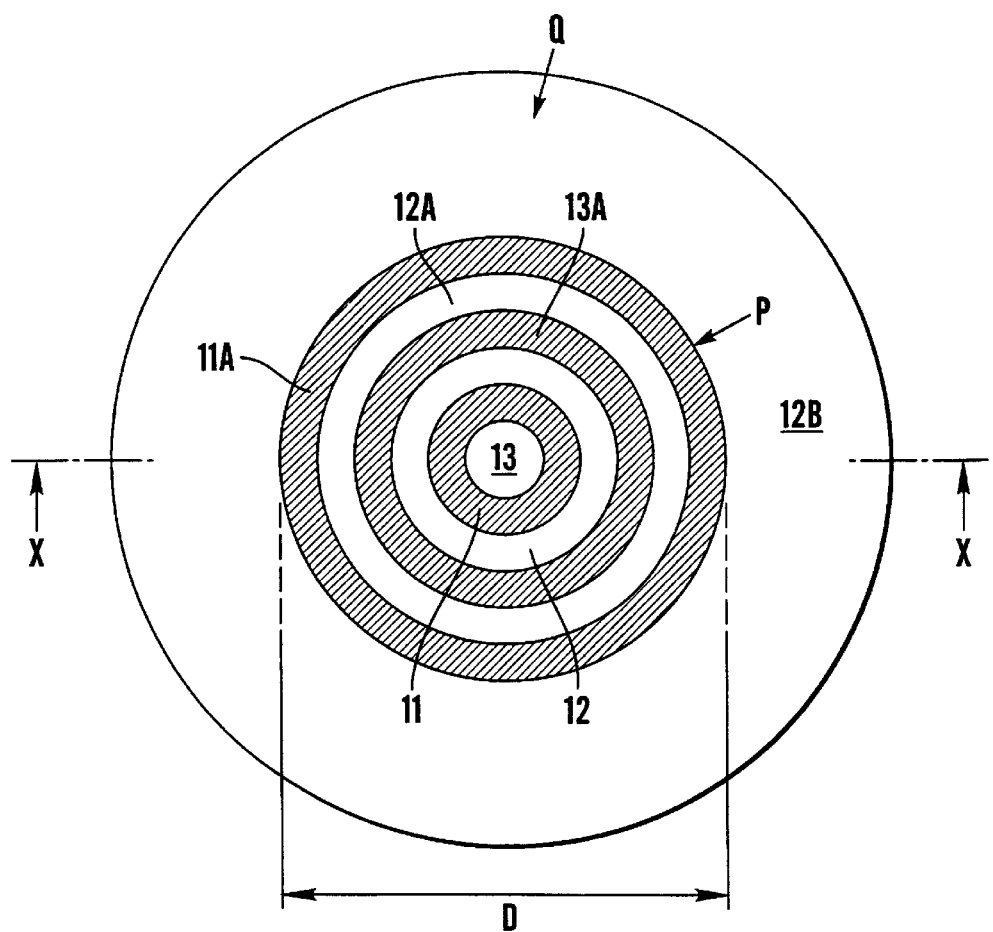
Figure 4:
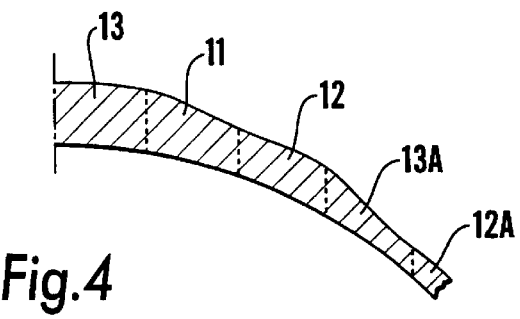

Various embodiments in accordance with the invention will now be described with reference to the accompanying drawings, in which:

FIG. 1 is a section through the viewing area of a contact lens in accordance with a first aspect of the invention, FIG. 2 is a similar section through the viewing area of a second embodiment of a contact lens in accordance with the first aspect of the invention, FIG. 3 is a plan view of a lens in accordance with the second aspect of the invention, and FIG. 4 is a part section on the line X—X in FIG. 3.

Referring to FIG. 1, the lens comprises an anterior power surface (1) and a posterior base curve (2). The lens has a central circular distance vision zone (3) formed in the posterior of the surface (2) and the central circular region is surrounded by a first concentric circular reading zone (4), having a radius appropriate to give a reading addition. A second concentric zone (5) for distance vision surrounds the first reading zone (4) having a refractive surface corresponding to that of the central zone (3). Further alternating, reading and distance vision zones (4') and (5') extend outwardly from the central area (3) so that, in total, the number of reading and distance vision zones in the major viewing area total at least 20.

Referring to FIG. 2, this shows a currently preferred embodiment which also has an anterior surface (1) and a base curve (2). In a similar fashion to the embodiment of FIG. 1, there is a central circular distance vision zone (3) and a series of closely spaced alternating reading and distance vision zones (4) and (5). However, in the case of the FIG. 2 embodiment, the reading zones are formed by providing zones which are flatter than the cornea, while the distance vision zones are formed from zones steeper than the cornea. The zones continuously merge one with the other, and by providing a very large number of zones, the effect of possible spurious reflections from the junction area (6) is reduced.

With the design shown in FIG. 2, half the reading addition effect is achieved by the portion which is flatter than the cornea (i.e. the reading zone) and the other half by the curve that is steeper than the cornea (i.e. the distance zone). In contrast, in the design shown in FIG. 1, the distance curvature approximately matches the corneal curve so that the entire reading effect is produced by the reading zones.

Lenses in accordance with the invention may be made from high water content soft lenses. Minus lenses often have a central thickness of the order of 0.06 mm. To avoid the tendency for the inner surface of the lens to be pressed onto the cornea, thus eliminating most of the effect of the reading addition, as well as giving a poor optical effect, it is desirable to reduce the thickness of the gap between the junction (6) and the cornea, where the lens is the greatest distance away from the cornea. Preferably, this distance should be less than about 0.007 mm, preferably between 0.003 and 0.006 or less.

It will be appreciated that by forming the reading correction on the rear surface of the lens, the same profile of the rear surface can be used with a variety of front surface curvatures, depending on the basic distance correction required. Thus, if the lenses in accordance with the invention are manufactured by casting a monomer composition, the same rear surface mould half can be used with a number of different front surface mould halves, thereby reducing the inventory required.

Lenses in accordance with the invention may be manufactured by machining or by moulding (casting). In the case of casting, the master moulds will be produced by machining the desired profile into the master mould half from which the casting moulds are produced.

In the case of the embodiment of FIG. 2, the zones are conveniently formed on the posterior lens surface by continuously changing the radius of the cutting tool.

Referring to FIGS. 3 and 4, these show a simplified version of a lens in accordance with a second aspect of the invention. The surface of a contact lens as shown in FIG. 3 has a major viewing area P consisting of a plurality of concentric zones and an outer area Q. The area P is shown in section in FIG. 4 and comprises a diameter which will cover the pupil over the range of light conditions.

Although the major viewing area P is divided into six zones, including a circular central zone (13), normally the central viewing area will be divided into a larger number of vision zones. As a minimum, there will be at least two zones of each character, i.e. distance or reading vision but, more commonly, the major viewing area will be divided into at least seven zones, for example, eleven to nineteen zones. There is, however, no absolute limit to the number of zones employed. Generally, better vision is experienced, the greater the number of zones as described above in relation to FIGS. 1 and 2.

As shown in FIG. 3, the central zone (13) is a distance vision zone and this is surrounded by further distance vision zones (12) and (12a) and by reading zones (11), (11a) and (13a). The outermost zone (12b) may also be a distance vision zone but, generally, will not take much part in the correction of the patient's optical defect, except in very dim light conditions.

The distance zone (13) at the centre of the lens does not have the same power as the corresponding distance vision zones (12, 12a) towards the periphery of the major viewing area (P). Instead, the distance vision zones progressively increase in their negative power towards the periphery. The increase may be progressive, for example, the first zone may be 0.25 dioptres more negative than the central zone (13), while the third zone may be 0.5 dioptres more negative, and the final zone (12b) may be a further 0.25 dioptres more negative so that it is 0.75 dioptres more negative than the central zone. The increase in negative power towards the periphery may, however, not necessarily be even, and several distance vision zones towards the periphery may have similar negative powers.

The reading zones may also increase in their negative power towards the periphery by the same or different degrees of negative power. Each reading zone may, for example, have the same reading addition in relationship to an adjacent distance vision zone so that effectively the reading zones become more negative towards the periphery. Alternatively in a lens complex design, the reading zones may have the same reading addition in relationship to the innermost distance vision zone.

FIG. 4 shows diagrammatically how the zones are cut in order to form alternate distance and reading refractive zones. These may be formed directly using a high precision computer-controlled lathe or, alternatively, the powers are cut onto the surface of the mould from which the lenses are produced.

Although, in the specific embodiment described above, the central zone is designed for distance vision and the adjoining annular zone for reading, it will be appreciated that the situation may be reversed.

Preferably, the lenses manufactured in accordance with this invention will be produced from material of the hydrated hydrophilic polymer type, so that the lenses are formed by machining or moulding a xerogel and the resulting products are then swollen by hydration in isotonic saline to produce the final lenses.

Although the invention has been described in connection with its application to the manufacture of bifocal lenses, it will be appreciated that the invention is also applicable to multi-focal lenses in which the vision zones may be divided into alternate near, intermediate and distance vision zones.

The annular zones and/or the basic power of the lens may be provided by refraction. However, the invention includes the use of diffractive rings to provide some or all of the power of the near or distance vision zones. In this connection, reference is made to U.S. Pat. No. 4,637,697 (Freeman) for details of the formation of diffractive power on a contact lens having basic refractive power.

What is claimed is:

1. A bifocal contact lens having a viewing area generally corresponding to the maximum pupil area of the wearer, said viewing area having a central circular refractive zone having a first focal length corresponding to distance vision or reading vision and a plurality of annular refractive zones which alternate between a second focal length and said first focal length corresponding to the other of reading and distance vision as they extend outwardly from said central zone, wherein at each pupil size between a minimum and a maximum the relative areas of the distance and reading zones are between 40:60 and 60:40, the total number of zones comprises at least 30, the zones are alternately flatter or steeper than the cornea and there is a progressive increase in negative power in at least some of the zones of the same character towards the periphery of the viewing area.

2. A lens according to claim 1 wherein the alternating zones are formed on the posterior lens surface.

3. A lens according to claim 2 wherein the maximum thickness of material removed between every other zone to form the zones is about 10% of the total thickness of the lens.

4. A lens according to claim 1 wherein the maximum tear thickness between the posterior lens surface and the cornea is about 0.007 mm.

5. A lens according to claim 1 wherein the zones are formed on the posterior lens surface by continuously changing the radius of the cutting tool.

6. A lens according to claim 1 wherein at least some of the distance vision zones have powers which progressively become more negative towards the periphery of the lens viewing area.

7. A lens according to claim 1 wherein at least some of the near vision zones have powers which progressively become more negative towards the periphery of the lens viewing area.

8. A lens according to claim 1 in which zones situated in the region of the periphery of the viewing area are more negative by a power of up to 0.75 dioptres than a zone of the same character situated close to the lens centre.

9. A lens according to claim 8 wherein zones situated in the region of the periphery of the viewing area are more negative by at least 0.25 dioptres than a zone of the same character situated close to the lens centre.

10. A lens according to claim 1 wherein at least one of the near or reading vision zones is aspherical.

11. A lens according to claim 1 wherein the surface area of the near (reading) vision zones is substantially equal to the surface area of the distance vision zones.

12. A lens according to claim 1 wherein at least some of the annular zones in a central region of the lens are formed concentrically about an optical centre which is spaced from the geometric centre of the lens so that in use the optical centre is offset nasally.

13. A lens according to claim 12 wherein the offset is about 0.3 to 2 mm.

14. A bifocal contact lens comprising a disc-like member having a concave surface and a viewing area on said surface, said viewing area including a central zone providing a distance or near vision correction, a plurality of concentric annular zones surrounding said central zone each providing, in alternation with increasing distance from said central zone, distance or near vision correction, the total number of zones being at least 30, the total area of the near vision zones being substantially equal to the total area of the distance vision zones, and said zones comprising depressions in said surface of generally equal depth and of a maximum depth of around 0.006 mm.

* * * * *